(12) United States Patent
Gross et al.

(10) Patent No.: US 11,642,547 B2
(45) Date of Patent: May 9, 2023

(54) BIORESONANCE FREQUENCY EMITTING DEVICE, SYSTEM, AND METHOD

(71) Applicant: WAVE FORCE ELECTRONICS INC., Victoria (CA)

(72) Inventors: Stuart Gross, Richmond (CA); James Gross, Coquitlam (CA); Stephen Davis, Mill Bay (CA); Henri Corniere, Vancouver (CA)

(73) Assignee: Wave Force Electronics Inc.

( * ) Notice: Subject to any disclaimer, the term of this patent is extended or adjusted under 35 U.S.C. 154(b) by 0 days.

(21) Appl. No.: 15/204,797

(22) Filed: Jul. 7, 2016

(65) Prior Publication Data

US 2017/0007847 A1    Jan. 12, 2017

Related U.S. Application Data

(60) Provisional application No. 62/189,974, filed on Jul. 8, 2015.

(51) Int. Cl.
*A61N 5/06* (2006.01)
*A61M 21/02* (2006.01)
*A61M 21/00* (2006.01)

(52) U.S. Cl.
CPC .......... *A61N 5/0624* (2013.01); *A61M 21/02* (2013.01); *A61M 2021/0044* (2013.01);
(Continued)

(58) Field of Classification Search
CPC .......... A61N 5/0624; A61N 2005/0659; A61N 2005/0661; A61N 2005/0662;
(Continued)

(56) References Cited

U.S. PATENT DOCUMENTS 4,883,067 A * 11/1989 Knispel ................ A61B 5/0482
600/545
5,458,142 A * 10/1995 Farmer .................... A61N 2/02
600/409

(Continued)

FOREIGN PATENT DOCUMENTS

| DE | 297 09 094 U1 | 9/1998 |
| DE | 102006011591 A1 | 9/2007 |
| EP | 2359900 A2 | 8/2011 |

OTHER PUBLICATIONS

EnglishTranslationRU2065297 (see attached) (Year: 1996).*

(Continued)

*Primary Examiner* — Sunita Reddy
(74) *Attorney, Agent, or Firm* — Marc Baumgartner; Baumgartner Patent Law

(57) ABSTRACT

A phototherapy or BRT process and apparatus is provided, which, using a pre-recorded bioresonance frequency or compilation of frequencies, causes an EMR emitter to emit within a biological window of a target organism to positively or negatively affect the organism. The EMR may be generated in one or more LEDs by a device connected to a controller of the EMR emitter which device provides the pre-recorded bioresonance frequency or compilation of frequencies to control the LEDs' emitted light in terms of its intensity and/or a frequency or flicker-rate.

4 Claims, 3 Drawing Sheets

Fig 2a

(52) U.S. Cl.
CPC . *A61M 2205/052* (2013.01); *A61M 2205/053* (2013.01); *A61M 2205/587* (2013.01); *A61N 2005/0651* (2013.01); *A61N 2005/0659* (2013.01); *A61N 2005/0661* (2013.01); *A61N 2005/0662* (2013.01)

(58) Field of Classification Search
CPC .......... A61N 2005/0651; A61M 21/02; A61M 2021/0044; A61M 2205/587; A61M 2205/052; A61M 2205/053
USPC ................. 600/26–28; 128/897–899; 607/88
See application file for complete search history.

(56) References Cited

U.S. PATENT DOCUMENTS

| | | | | |
|---|---|---|---|---|
| 5,830,140 | A * | 11/1998 | Dillinger | A61K 41/0004 600/407 |
| 6,528,954 | B1 | 3/2003 | Lys et al. | |
| 6,541,978 | B1 | 4/2003 | Benveniste et al. | |
| 2002/0047646 | A1 * | 4/2002 | Lys | H05B 33/0803 315/312 |
| 2002/0057061 | A1 * | 5/2002 | Mueller | G09G 3/14 315/291 |
| 2002/0138099 | A1 * | 9/2002 | Markin | A61N 1/3603 607/1 |
| 2002/0138118 | A1 * | 9/2002 | Debrouse | A61N 1/40 607/72 |
| 2003/0028260 | A1 * | 2/2003 | Blackwell | H05B 33/0803 700/18 |
| 2003/0100837 | A1 * | 5/2003 | Lys | A61N 5/0616 600/476 |
| 2004/0267333 | A1 * | 12/2004 | Kronberg | A61N 1/36021 607/72 |
| 2005/0248962 | A1 | 11/2005 | Searfoss | |
| 2007/0206375 | A1 * | 9/2007 | Piepgras | A43B 1/0027 362/147 |
| 2008/0039905 | A1 * | 2/2008 | Tomescu | A61N 1/3603 607/66 |
| 2009/0187232 | A1 * | 7/2009 | Salim | A61B 5/05 607/46 |
| 2010/0016783 | A1 * | 1/2010 | Bourke, Jr. | A61P 35/00 378/65 |
| 2010/0072996 | A1 * | 3/2010 | Jacobson | A61N 2/002 324/309 |
| 2010/0174222 | A1 * | 7/2010 | McDaniel | A61K 41/0057 424/59 |
| 2011/0208258 | A1 * | 8/2011 | Rasnetsov | A61N 5/00 607/3 |
| 2012/0310703 | A1 * | 12/2012 | Cavalcanti | G06Q 30/0201 705/7.29 |
| 2013/0131537 | A1 * | 5/2013 | Tam | A61B 5/4854 600/544 |
| 2014/0128941 | A1 | 5/2014 | Williams | |
| 2015/0297109 | A1 * | 10/2015 | Garten | A61B 5/04845 600/544 |
| 2016/0361416 | A1 * | 12/2016 | Taylor | A61K 33/00 |
| 2018/0043175 | A1 * | 2/2018 | Karpf | A61N 2/008 |
| 2019/0373687 | A1 * | 12/2019 | Williams | A61N 5/06 |
| 2020/0222711 | A1 * | 7/2020 | Walder | A61K 41/0066 |

OTHER PUBLICATIONS

Tsen KT, Tsen SW, Fu Q, Lindsay SM, Kibler K, Jacobs B, Wu TC, Karanam B, Jagu S, Roden RB, Hung OF, Sankey OF, Ramakrishna B, Kiang JG. Photonic approach to the selective inactivation of viruses with a near-infrared subpicosecond fiber laser. J Biomed Opt. Nov.-Dec. 2009;14(6):064042. (Year: 2009).*

Advanced Medical Systems' Wave Transfer C; https://www.magnetotherapy.de/our-products/devices-for-therapists/wave-transferc/wave-transfer-c.html; PDF retrieved Dec. 2, 2019.

Digital Homeopathy; http://www.tachyon-aanbieding.eu/Documentation/Digital%20Homeopathy.pdf; PDF retrieved Dec. 2, 2019.

Marko S Markov: ""Biological Windows": A Tribute to W. Ross Adey", The Environmentalist, Kluwer Academic Publishers, BO, vol. 25, No. 2-4, Dec. 1, 2005 (Dec. 1, 2005), pp. 67-74, XP019240262, ISSN: 1573-2991, DOI: 10.1007/S10669-005-4268-8.

* cited by examiner

Static Model

Electronic Schematic

Dynamic Model

Electronic Schematic

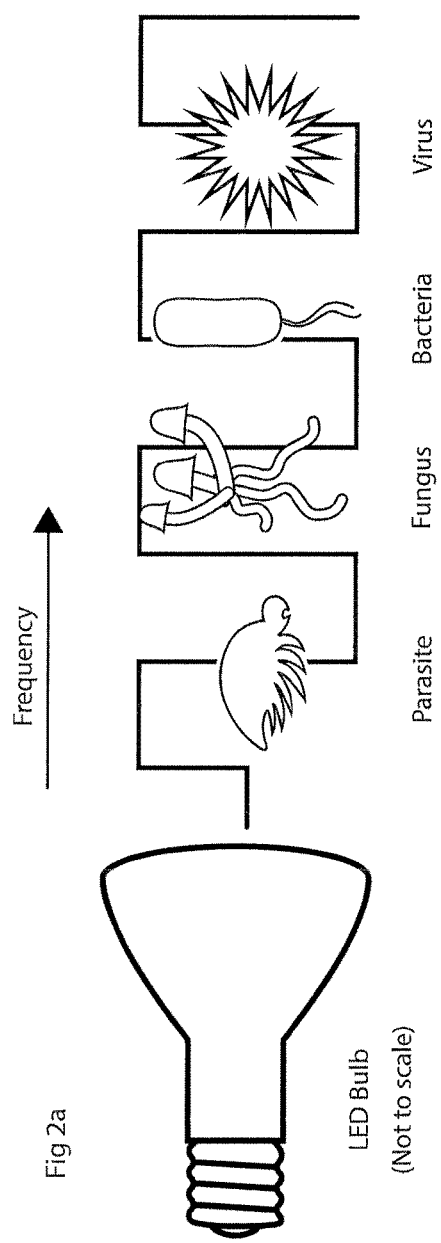
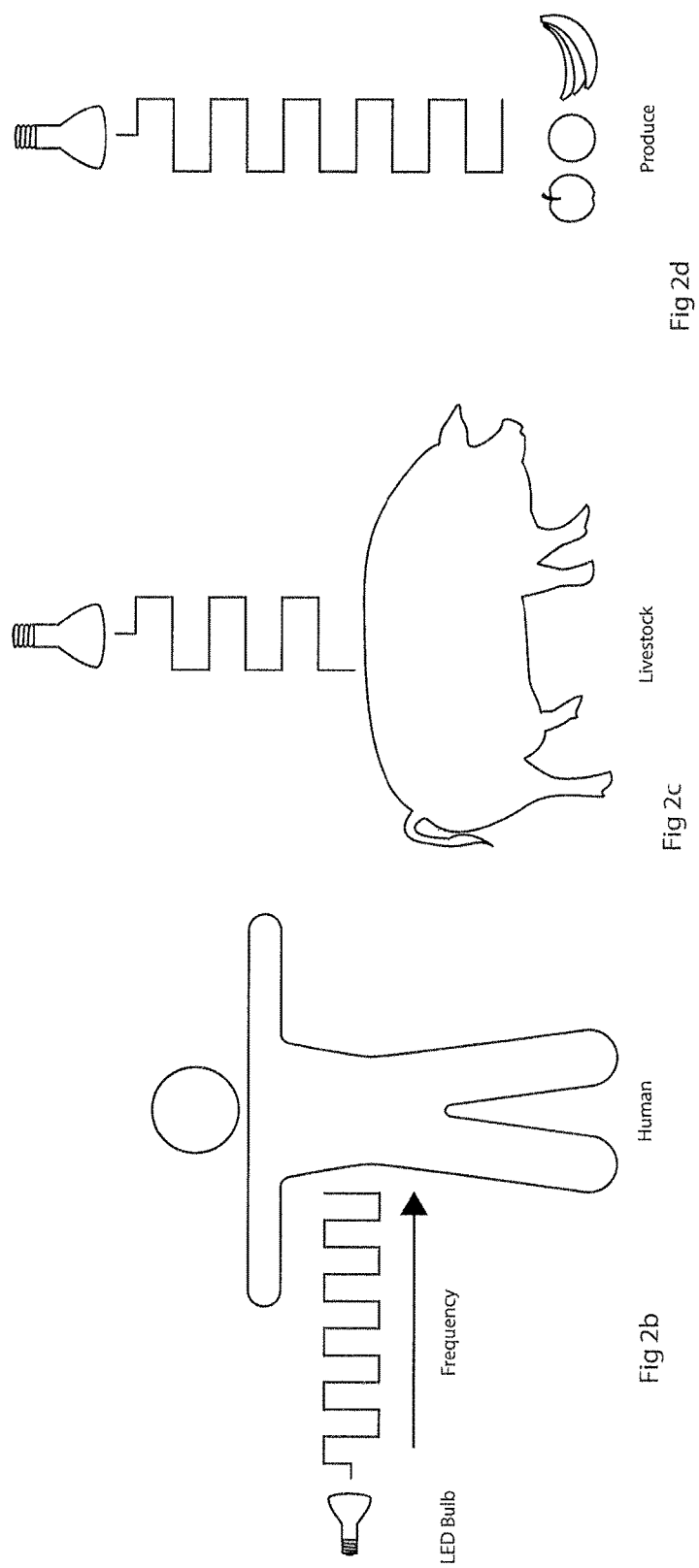

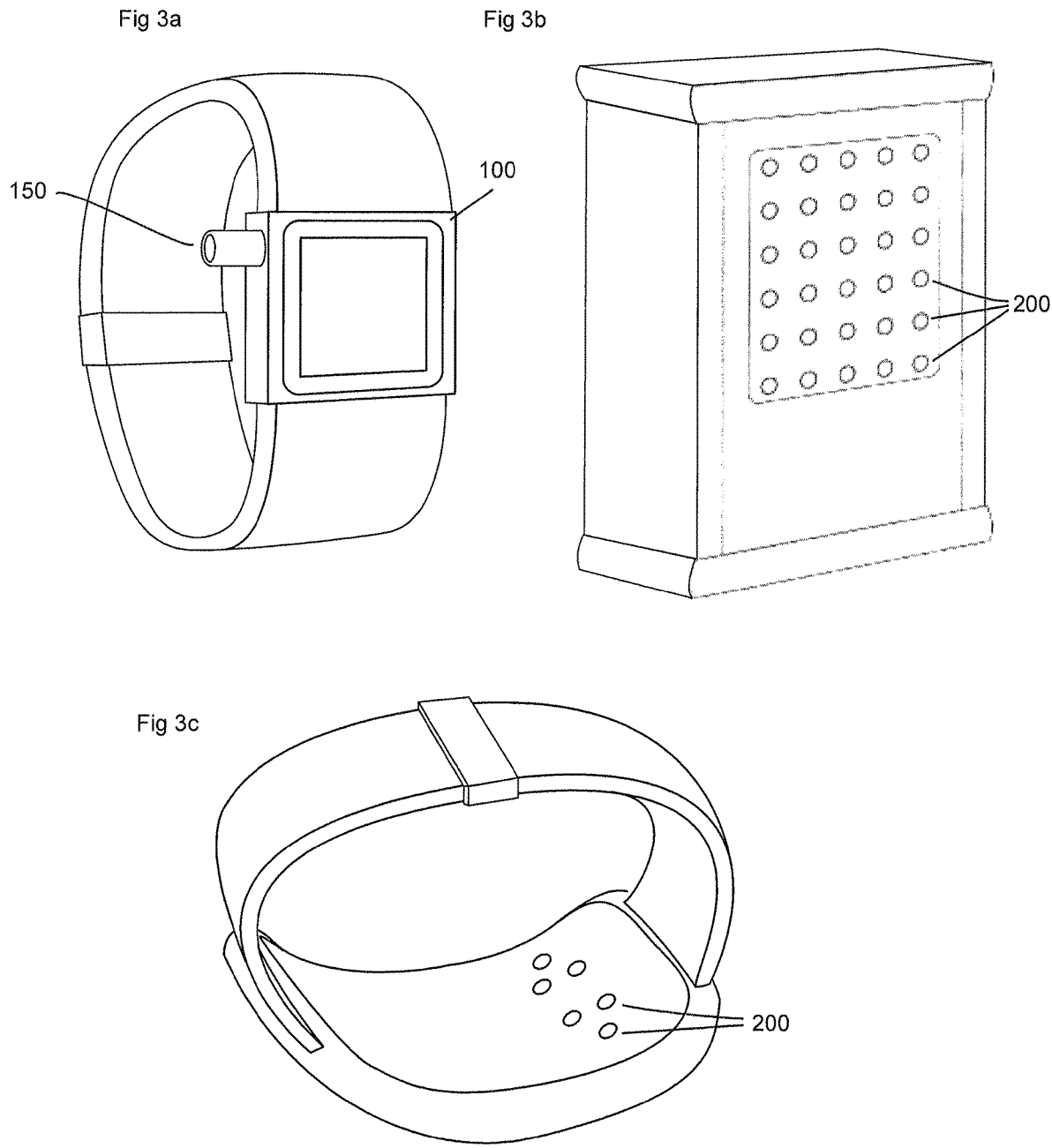

BIORESONANCE FREQUENCY EMITTING DEVICE, SYSTEM, AND METHOD

FIELD OF THE INVENTION

The present invention relates to devices, systems, and methods for selectively emitting bioresonance frequencies to induce a biological effect.

BACKGROUND OF THE INVENTION

Discussion of Prior Art

Perhaps the closest prior art of which Applicant is aware is the disclosure in US Patent Application Publication US2014/0128941 A1 of Richard K. Williams, entitled "Phototherapy System and Process Including Dynamic LED Driver with Programmable Waveform" (Williams '941). Williams '941 discloses a wealth of knowledge about how ElectroMagnetic Radiation (EMR) may be applied to living organisms as a therapy, in other words, to induce a biological effect. Williams '941 discusses and discloses how to generate specific EMR emissions having specific programmed characteristics (of frequency, amplitude, pulse length and spacing, etc.) using a microcontroller and a library of algorithms each of which is applied to generate specific synthetic EMR emissions.

The prior art system (Williams '941 in particular) has several shortcomings, namely: i) the synthetic EMR emissions have characteristics which are not naturally derived; ii) the algorithms used to generate the synthetic EMR emissions are of necessity simplifications and approximations, and so the EMR emissions will be simpler than naturally occurring EMR such as EMR found in natural environments or associated with physical objects or sources in the real world; and iii) systems such as Williams '941 require storage for algorithm libraries, microprocessor devices, and additional equipment to turn signals from the microprocessor responsive to the algorithm(s) into instructions for an EMR emitter. This is complex, typically run on digital equipment and has in-built approximations in the algorithms and in their processing and resultant signals, and is overly complex and expensive.

SUMMARY OF THE INVENTION

It is an object of this invention to overcome at least some of the disadvantages of the prior art.

An EMR emitter for bioresonance therapy is provided in one embodiment of the invention, comprising: an input to receive a pre-recorded pattern; an emitter controller to change the intensity or luminance, or the pulse-width of the emitter's emission proportionately to the pre-recorded pattern.

An emitter is provided in another embodiment where the EMR emission comprises infrared (IR), near-IR, visible or ultraviolet (UV) light.

Another embodiment provides an emitter where the emitter's patterned emission is in a biological window of a target organism; and the patterned emission from the emitter is beneficial to the target organism. Examples of beneficial effects may include changes to stress and anxiety levels, sleep patterns, psychological mood, or some physiological functions. In another case, the patterned emission from the emitter is detrimental to the target organism and the target organism to be detrimentally affected is a disease-causing organism. In such as case, the target organism may be one of: a parasite, a virus, bacteria, mold, or amoebae, or is a cause of a particular disease.

In one embodiment, the target organism is a cause of Lyme's disease and co-infections that are related to Lyme disease.

A further embodiment provides a method of tailoring EMR for bioresonance therapy comprising providing a pre-recorded pattern to an EMR emitter, which causes the emitter to emit EMR within a biological window of a target organism, the EMR emission pattern being reflective of the pre-recorded pattern by having the emitter's EMR emission change in intensity or luminance, or changing the pulse-width of the emitter's emission, proportionately to the pre-recorded pattern, and applying the patterned EMR emission to a member of the target organism's class.

The present invention is not to be limited by the description either here or in the detailed description below, which are merely examples—upon reading these descriptions, those skilled in the art will recognize various modifications thereof, and it is therefore to be understood that such modifications are intended to fall within the scope of the appended claims and their legal equivalents.

BRIEF DESCRIPTION OF THE DRAWINGS

The invention will now be described by way of an exemplary embodiment with reference to the accompanying, diagrammatic, not-to-scale drawings. Any dimensions provided in the drawings are provided only for illustrative purposes, and do not limit the invention as defined by the claims. In the drawings:

FIG. 2a is a schematic diagram illustrating a wave form that can be emitted by the device according to one embodiment of the present invention;

FIG. 2b is a schematic diagram illustrating the application of the device on a human;

FIG. 2c is a schematic diagram illustrating the application of the device on livestock; and FIG. 2d is a schematic diagram illustrating the application of the device on produce.

FIG. 3 shows several instances of EMR emitter devices: 3a is an audio player with emitter plug for insertion into 3.5 mm stereo audio output jack; 3b is an LED panel; 3c is a form of wearable device with pre-recorded files loaded into memory on board either wirelessly or by wired connection to control the device's EMR emission patterns.

DETAILED DESCRIPTION OF THE INVENTION

Figure 1A:
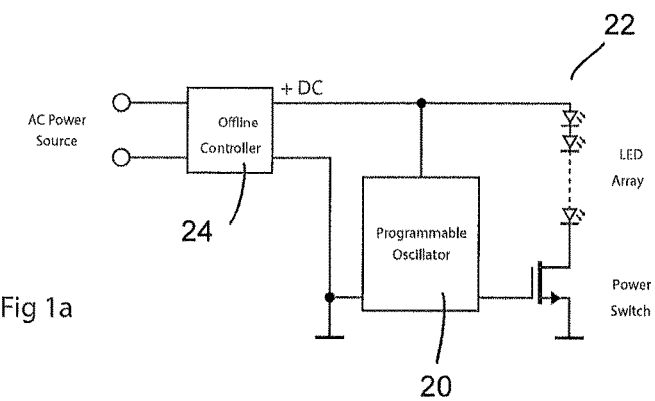
FIG. 1a is a schematic diagram of the circuitry of a device according to one embodiment to the present invention.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

At the smallest level, every element is composed of sub-atomic particles. These fundamental building blocks radiate waves of energy (i.e. vibration and/or wave form) in unique patterns that are combined to make up everything around us. All things, including water and minerals, animals, bacteria, viruses, and chemicals are all composed of specific combinations of vibrating energy.

Bioresonance Therapy (BRT) is a healing modality that uses electromagnetic energy, transmitted to a living organism, for the purpose of restoring the biological systems and organs to their normal energetic state. Vibrational energy, like electromagnetic energy, is also produced by moving particles that transfer their energy from one to another. Vibrational energy may be used in bioresonance therapy to transmit energy (at selected frequencies) to biological systems and organs for various purposes.

When an organ becomes unhealthy, its typical resonant frequency may change. If this organ is being affected by pathogens, BRT may disrupt them by transmitting specific frequencies to the body that have been shown to be effective in interrupting or interfering with the pathogenic agent: bacteria, viruses, fungi, etc. (see FIG. 2a).

The bioresonance principle may also apply to pest control. For example, by exposing microbes to the appropriate resonant frequencies, pests may be eliminated as they absorb specific energy that disrupts their normal function.

The cells of the human body vibrate, or oscillate. This can be seen in video footage of red blood cells traveling through vessels under high magnification, or macrophages chasing bacteria. Electromagnetic impulses of the appropriate frequencies can produce cellular resonance—vibration at maximum amplitude. As with the cell, electromagnetic impulses produce resonant vibrations of these membrane receptors (neuropeptides) to stimulate a variety of functions within the cell. There are approximately 75 trillion cells in the human body. Each cell membrane has over 1 million neuropeptide receptors. An electromagnetic field applied within the biological window, signals all of these receptors simultaneously at the speed of light. One can picture the cellular resonance produced—all cells vibrating and oscillating in phase. This is the essence of magnetic resonance stimulation. The profound beneficial effects in human physiology through magnetic resonance may be produced through improved intercellular communication and intracellular interactions produced through the induction of resonance in the body. The new generation of magnetic field therapy systems targets the extremely low frequency range—matching known tonic oscillatory frequencies of the body's cells.

Subtle energies, such as extremely low frequency (ELF) magnetic waves, have profound effects on human physiology. One dramatic effect is the positive influence of pulsed magnetic fields on depleted bone density. To understand how this happens, we need to understand that we are dealing with waves. Waves have amplitude (strength) and frequency (which is determined by wavelength). Waves summate (adding together to become larger in amplitude) and they can also negate one another, thereby reducing amplitude. A simple example of this is the physics of sound waves. Harmony is the matching of two separate tones along the same wavelength; the two tones are combined. When their wavelengths and frequencies are in synchrony, we experience a pleasant sensation: a harmonic chord. Disharmony (e.g., music that is hard to listen to and "off key") occurs when separate tones have different wavelengths and don't match up with one another.

Carrying this musical example further, a musical "overtone" occurs when harmonies are added upon one another in perfect mathematical relation. The harmonic chord is heard, and the overtone is heard as well. The overtone is heard, but has not been sung or played by an instrument. This is an example of "resonance," or more precisely, "stochastic resonance." The overtone is not produced directly; it is derived through the frequency of sound waves vibrating (or oscillating) in harmony. This principle is fundamental to a proper understanding of magnetic waves and magnetic field therapy. Synchronous oscillation of electromagnetic waves is called resonance. Resonance is not produced directly, but is derived through a summation of electromagnetic vibrations within the cells of the body. The induction of cellular resonance—synchronous biomagnetic vibrations in the body—creates the biological window necessary to produce a healing response in the tissues. Using a proper dosage of pulsed EM waves in an optimal pattern, a biological harmonic "overtone" is created and membrane receptors of poorly functioning cells in the body begin to vibrate at a frequency of health. Through a variety of physiological mechanisms, effects such as improved circulation and enhanced cellular regenerative response may be achieved, resulting in healthy cell function to be restored and overall health improved.

Harmonic oscillations are frequencies that develop as a multiple of the fundamental (or tonic) frequency—similar to the upper harmonics (or "overtones") in music. For example, rectangular impulses with a fundamental oscillation of 1 Hz simultaneously create upper harmonics of 3, 5, and 7 Hz etc. Upper harmonics to the 2nd upper harmonic has the same strength as the fundamental oscillation.

In order to create resonance, the field strengths (electromagnetic amplitude) and pulse frequencies (wavelengths) utilized should match the biological window being accessed. Mathematical calculations of probability are used to determine which field strengths and amplitudes are likely to induce the greatest resonance and therefore the most beneficial biological window for magnetic resonance stimulation.

To restate the principle of resonance yet another way, if the intensities and field strengths used in applying magnetic resonance stimulation are similar to those of the biological window, a stochastic amplification may create beneficial biological effect.

Rectangular impulses have a steep ascending and descending phase (sharp rise time and fall time). They create harmonics at odd-numbered frequencies (e.g., 3, 5, 7, and 9 Hz). The result is that they are likely to produce greater energetic resonance of the cells and body tissues.

The present invention relates to devices, systems, and methods for selectively emitting bioresonance frequencies to induce a biological effect. There are a number of possible applications for this invention, including, for example, to promote healing in a health-care setting (see FIG. 2b); to encourage mental focus and concentration in an educational or business setting. Other examples of beneficial effects may include changes to stress and anxiety levels, sleep patterns, psychological mood, or some physiological functions. Similarly, the effects may be to neutralize bacteria or deter bacteria growth in a food storage or food processing setting (see FIG. 2d); to neutralize parasites, viruses, and bacteria in an agricultural setting (See FIGS. 2a and 2c). For example, a frequency of 107.88 Hz may be used to neutralize viruses.

In a sample embodiment, with reference to FIGS. 1a to 1d, a device of the present invention may be connected to a conventional light socket and/or fixture. The device may be integrated with a light source which, for example, may be a light bulb comprised of an LED array. Other light sources are possible.

Figure 1B:
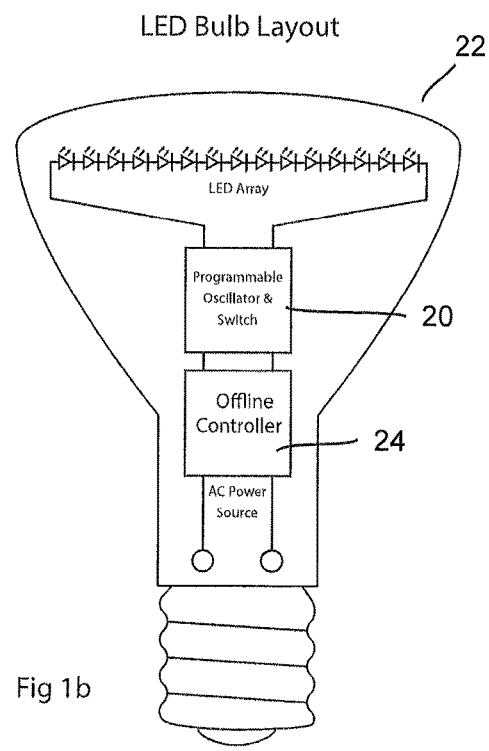
FIG. 1b is a schematic diagram showing the device of FIG. 1a integrated with a light source.

In one embodiment, with reference to FIGS. 1a and 1b, the device of the present invention comprises a programmable oscillator [20] connected to a solid state light source [22]. The oscillator [20] is used for changing the standard frequency of the light source to a specific different frequency by changing the frequency at which the light source oscillates. In the sample illustrated embodiment, the light source is an array of light emitting diodes (LEDs). The oscillator, which may be programmed by precision resistors, is used to switch the LEDs on/off at a predetermined low frequency (e.g. in the hundreds of Hz range, for example 107.88 Hz), which cannot be changed subsequently. This embodiment is referred to herein as the "static model".

The oscillator is connectable to a power source, such as an AC power source (e.g. from a light bulb socket), via an offline controller 24. The offline controller is for transforming AC current to a direct current (DC), if the device and/or the oscillator are configured to receive power from an alternating current (AC) source, and/or for adjusting the voltage of the current source as required for use by the oscillator.

Figure 1C:
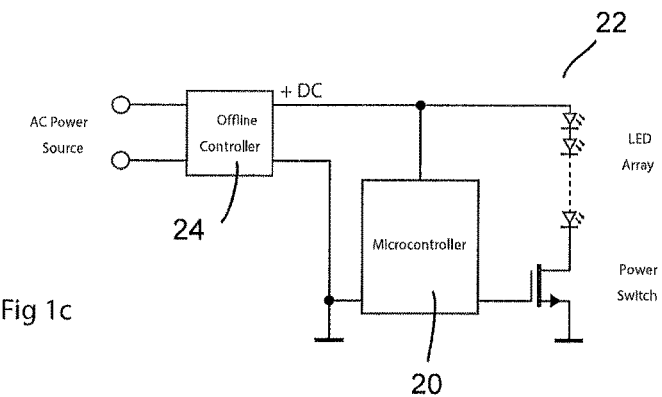
FIG. 1c is a schematic diagram of the circuitry of a device according to another embodiment of the present invention.
Figure 1D:
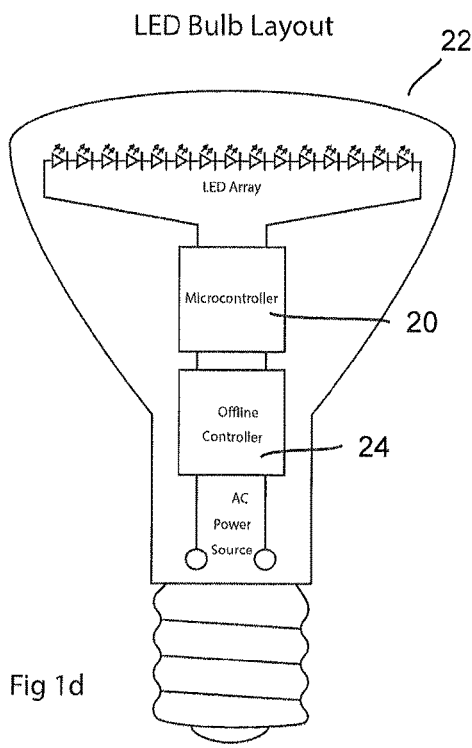
FIG. 1d is a schematic diagram showing the device of FIG. 1c integrated with a light source.

In another sample embodiment, with reference to FIGS. 1c and 1d, a device of the present invention comprises a microcontroller [120] in communication with a solid state light source [22]. The microcontroller may, for example, be a microchip and/or integrated circuit (IC) that is integrated with the light source or part of the IC. The microcontroller is used for changing the standard frequency of the light source to a specific different frequency by changing the frequency at which the light source oscillates. In the sample illustrated embodiment, the light source is an array of light emitting diodes (LEDs).

In a preferred embodiment, the microcontroller can be remotely manipulated by an external remote controller (not shown) via a wireless connection such that the oscillations emitted by the light source can be changed upon receipt of a command or a pre-recorded signal from the external remote controller. This embodiment is referred herein as the "dynamic model". For example, the microcontroller may be integrated into the circuitry of the light source as shown in FIGS. 1c and 1d.

The microcontroller is connectable to a power source, such as an AC power source (e.g. from a light bulb socket), via the offline controller [24]. The offline controller is for transforming AC current to a direct current (DC), if the device and/or the microcontroller are configured to receive power from an alternating current (AC) source, and/or for adjusting the voltage of the current source as required for use by the microcontroller.

The remote controller is a device capable of emitting an electronic signal wirelessly via a communication network, such as the Internet, a cellular phone network, Bluetooth connection, or a Wi-Fi connection. The remote controller may be for example a smart phone, a mobile phone, a personal computer, etc. To change the oscillations emitted by the light source, the remote controller sends a command code that is received by the microcontroller and the microcontroller changes the oscillations of the light source.

The dynamic model allows a user to select, via the remote controller, the frequencies to be emitted by the device.

In one embodiment, the device may be manufactured by integrating a microcontroller with an existing light source, for example, a conventional LED lamp. The array of LED's in a conventional LED lamp is usually powered by a DC voltage and current supplied by a controller.

In one embodiment, the programmable oscillator has a programmable period, which normally generates a square wave (with a 50% duty cycle). The programming of the oscillator is set by resistors to generate an oscillation frequency. The output frequency of the static model is controlled by a fixed resistor and does not change. The dynamic model uses the microcontroller to determine the output frequency and the microcontroller can be controlled remotely by the remote controller, or directly onboard the device, by providing pre-recorded signals to control the EM emitter's emissions.

The oscillator in the static model, or the microcontroller in the dynamic model, in turn controls a power MOSFET transistor (also sometimes referred to herein as the "switch") which drives the LED array at the frequency set by the resistors or responsive to the pre-recorded EM frequency desired. The device may include a low voltage, low power positive regulator for controlling the amount of input voltage to the oscillator or the microcontroller, whichever is applicable, since the oscillator or microcontroller may not be capable of receiving the same voltage that is necessary to power the LEDs (e.g. about 30V). If the oscillator or microcontroller requires an input voltage that is lower than that of the power source (e.g. an AC power outlet), the input voltage to the oscillator or microcontroller can be reduced by the regulator.

The input voltage required for the LEDs may be higher than that of the oscillator or microcontroller, and may be the same as that of the power source. As such, the input voltage required for the LEDs may be supplied directly by the power source and may not be controlled by the regulator.

The device is preferably small enough that it can be easily fitted into a socket (i.e. the Edison screw) of conventional LED bulbs or portable light sources, such as a flashlight, or connected to a wearable device, player or smartphone to use the connected device as an emitter.

Depending on the values of the resistors and the pre-recorded EM signals, the frequency emitted by the device can be varied. The resistance value (R) used to control the frequency output is determined by the programmable oscillator in use.

It is to be noted that in at least a preferred embodiment, the EMR emitter is controlled by signals provided from another device, whether wired or wirelessly connected, in order to provide the pattern of EMR emission to be emitted by the emitter. In this respect, the above descriptions and the associated electronics will be much simplified, with a pre-recorded emission pattern being provided to drive the electronics to drive the EMR emitter (in these examples LEDs) to emit a particular pre-recorded pattern. Note that the pre-programmed emission pattern can be stored locally on the device.

In these embodiments, a bioresonance frequency or a compilation of frequencies may be recorded and stored as a digital audio file in various formats, such as for example .mp3, .wav, .aiff, .m4p, .m4a, .wma, etc. The digital audio file may be played by an audio player. The audio device may be connected to audio or EMR emitter devices.

In another embodiment, a digital audio file comprising a bioresonance frequency or a compilation of frequencies may be transformed into an audio signal by a conventional audio player. The audio signal may be converted to EMR emissions tailored by the audio signal, and broadcasted by a transmitter that is connectable to the audio player via, for example, a headphone jack, an aux input jack, USB connection, or similar connections. The transmitter broadcasts the audio signal as electromagnetic waves. See FIG. 3 which shows a wristband audio player 100 with an EMR emitting dongle 150 plugged into the player's audio-out jack. The EMR emitter may be a panel of LEDs as in FIG. 3b at 200, or may be LEDs or emitters 200 contained in a wearable device, as in FIG. 3c.

It is these last embodiments which are of most interest, in that the EMR emitter device of the invention, in the 'dynamic model' can be controlled by a pre-recorded bioresonance frequency or compilation of frequencies. The bioresonance frequency or compilation of frequencies will have been pre-recorded using methods and systems, sensors and devices, known to those skilled in the art of BRT. In certain cases, the recorded bioresonance frequency or compilation of frequencies, may be recorded by subjecting an isolated sample of a known substance of interest to known stimulae in a controlled setting, and recording resulting frequencies or compilations of frequencies for that substance of interest over time. In this way, a bioresonance frequency or compilation of frequencies which may provide useful effects on a target organism when used to control an EMR emitter's emissions within a biological window for an organism, may be derived directly from a natural source or the substance of interest, rather than synthesized from theory or some other source. It is thought that these naturally sourced pre-recorded bioresonance frequencies or compilations of frequencies are more complex and may be more effective than simpler or differently derived or synthesized EMR emissions when used to drive EMR emissions for BRT.

Additionally, by providing the EMR emitter with pre-recorded patterns to drive EMR emissions, the EMR emitter device may be made much simpler, having only to convert signals in the pre-recorded patterns to a substantially similar EMR emission pattern, and not requiring memory, algorithmic interpretation and synthesizing of artificial EMR emission patters.

The present invention is not to be limited by the description either here or in the detailed description below, which are merely examples—upon reading these descriptions, those skilled in the art will recognize various modifications thereof, and it is therefore to be understood that such modifications are intended to fall within the scope of the appended claims and their legal equivalents.

As will be apparent to those skilled in the art, various modifications, adaptations and variations of the foregoing specific disclosure can be made without departing from the scope of the invention claimed herein.

The invention claimed is:

1. A bioresonance therapy electro-magnetic radiation (EMR) system for inducing synchronous biomagnetic vibrations within a biological window of a target organism, the EMR system comprising:
   a. a pre-recorded EMR pattern, the pre-recorded EMR pattern consisting of a pulse frequency or a compilation of pulse frequencies emanated from a single natural source, is unmodified and is within the biological window of the target organism, the pre-recorded EMR pattern having a signal or signals therein;
   b. an EMR emitter configured to receive the signal or signals, to convert the signal or signals into a similar EMR emission pattern as the pre-recorded EMR pattern and to emit the similar EMR pattern, wherein the EMR emitter is at least one light emitting diode, and wherein the similar EMR emission pattern comprises IR (Infrared), near-IR, visible or UV (ultraviolet) light;
   c. an emitter controller, the emitter controller configured to receive the pre-recorded EMR pattern and to adjust an amplitude of an emission from the at least one light emitting diode to generate the similar EMR emission pattern, wherein the light emitting diode emits the similar EMR pattern, wherein the light emitting diode does not receive the signal or signals and does not convert the signal or signals into the similar EMR emission pattern, wherein the emitter controller is configured to switch the at least one light emitting diode on and off at 107.88 Hertz, with the emitted EMR pattern effecting the synchronous biomagnetic vibrations in the target organism, wherein the similar EMR emission pattern is detrimental to the target organism, and wherein the target organism is a virus.

2. The system of claim 1, wherein the emitter controller is a programmable oscillator.

3. A bioresonance therapy EMR method for providing bioresonance therapy to a target organism, the method comprising:
   a. providing a pre-recorded EMR pattern to an EMR emitter, the EMR pattern consisting of a pulse frequency or a compilation of pulse frequencies which emanated from a single natural source, is unmodified and is within a biological window of the target organism, the pre-recorded EMR pattern having a signal or signals therein;
   b. the EMR emitter receiving the signal or signals, wherein the EMR emitter is at least one light emitting diode;
   c. the EMR emitter converting the signal or signals into a similar EMR emission pattern as the pre-recorded EMR pattern via an emitter controller that receives the pre-recorded EMR pattern and adjusts an amplitude of an emission from the EMR emitter to generate the similar EMR emission pattern, wherein the EMR emitter emits the similar EMR pattern, wherein the light emitting diode does not receive the signal or signals and does not convert the signal or signals into the similar EMR emission pattern, and wherein the similar EMR emission pattern comprises IR, near-IR, visible or UV light, wherein the emitter switches the at least one light emitting diode on and off at 107.88 Hertz;
   d. the EMR emitter emitting the similar EMR pattern to the target organism, wherein the similar EMR emission pattern is detrimental to the target organism, and wherein the target organism is a virus; and
   e. the similar EMR pattern inducing synchronous biomagnetic vibrations in the target organism, and wherein the synchronous biomagetic vibrations provide bioresonance therapy to the target organism.

4. The method of claim 3, further comprising recording an EMR pattern from the natural source to provide the pre-recorded EMR pattern.

* * * * *